United States Patent
Plassman et al.

(10) Patent No.: US 9,861,782 B2
(45) Date of Patent: Jan. 9, 2018

(54) VARIABLE STIFFNESS CATHETER

(71) Applicant: Cook Medical Technologies, LLC, Bloomington, IN (US)

(72) Inventors: Trevor Plassman, Bloomington, IN (US); Logan Michael Cage, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 106 days.

(21) Appl. No.: 15/095,465

(22) Filed: Apr. 11, 2016

(65) Prior Publication Data

US 2016/0220787 A1 Aug. 4, 2016

Related U.S. Application Data

(62) Division of application No. 14/207,294, filed on Mar. 12, 2014, now Pat. No. 9,370,639.

(60) Provisional application No. 61/777,447, filed on Mar. 12, 2013.

(51) Int. Cl.
*A61M 25/00* (2006.01)

(52) U.S. Cl.
CPC .... *A61M 25/0053* (2013.01); *A61M 25/0054* (2013.01)

(58) Field of Classification Search
CPC .......... A61M 25/0053; A61M 25/0054; A61M 25/0026; A61M 25/0012; A61M 2025/0004
See application file for complete search history.

(56) References Cited

U.S. PATENT DOCUMENTS

| | | | |
|---|---|---|---|
| 4,236,509 A | 12/1980 | Takahashi et al. | |
| 4,728,319 A | 3/1988 | Masch | |
| 5,176,660 A * | 1/1993 | Truckai | A61M 25/005 138/123 |
| 5,234,437 A | 8/1993 | Sepetka | |
| 5,271,415 A | 12/1993 | Foerster et al. | |
| 5,409,470 A | 4/1995 | McIntyre et al. | |
| 5,454,795 A | 10/1995 | Samson | |
| 5,695,483 A | 12/1997 | Samson | |
| 5,951,539 A | 9/1999 | Nita et al. | |
| 6,890,329 B2 | 5/2005 | Carroll et al. | |
| 7,850,623 B2 * | 12/2010 | Griffin | A61M 25/0013 600/585 |
| 8,246,536 B2 | 8/2012 | Ochi et al. | |
| 2001/0041881 A1 | 11/2001 | Sarge et al. | |
| 2006/0129130 A1 | 6/2006 | Tal et al. | |
| 2012/0277729 A1 | 11/2012 | Melsheimer | |

* cited by examiner

*Primary Examiner* — Rebecca E Eisenberg
(74) *Attorney, Agent, or Firm* — Brinks Gilson & Lione

(57) ABSTRACT

A variable stiffness catheter having two concentric coils. A first coil is fixed with relation to the body of the catheter and a second coil is able to rotate in the space between adjacent turns of the first coil. The second coil translates axially in response to being rotated. When the second coil is advanced to its distal position, the stiffness is maximized. When the second coil is retracted proximally, the stiffness of the coil is reduced.

6 Claims, 5 Drawing Sheets

VARIABLE STIFFNESS CATHETER

RELATED APPLICATIONS

The present patent document is a continuation of application Ser. No. 14/207,294, filed Mar. 12, 2014, which claims the benefit of the filing date under 35 U.S.C. §119(e) of Provisional U.S. Patent Application Ser. No. 61/777,447 filed Mar. 12, 2013, which is hereby incorporated by reference.

FIELD

Embodiments of the present invention generally relate to medical devices and more particularly to wire guides and catheters for use in peripheral intervention.

BACKGROUND

Wire guides are commonly used in vascular procedures, such as angioplasty procedures, diagnostic and interventional procedures, percutaneous access procedures, and radiological and neurological procedures. In general, wire guides may be used to introduce a wide variety of medical devices into the vascular system.

Generally, during each of the foregoing procedures, a wire guide is first inserted into a patient's vascular system and is then advanced toward a target site. Various wire guides comprise flexible distal regions to facilitate navigation through the tortuous anatomy of a patient's vasculature. Where such flexible distal regions are used, it may be difficult to insert a medical component over the wire guide because of the flexibility of the distal region. However, if the distal region is too stiff, then it may be too difficult to advance the wire guide to the target site.

In order to facilitate advancement of medical component to the target site, some medical procedures utilize two wire guides, a first flexible wire guide for initially traversing the vasculature, and then a stiffer wire guide is advanced over or along the side of the initial wire guide. Once the stiffer wire guide is in place, a catheter can then be advanced over the stiffer wire guide. This procedure works well, but requires three different components be advanced through the vasculature of the patient.

It would be beneficial to have a single component that could function as both a wire guide and a catheter, such that a single procedure could be used to guide a catheter to a target area. Such a component would need to be flexible to navigate the tortuous anatomy of a patient, yet would also need to be stiff to facilitate pushability of the component.

SUMMARY

In one embodiment of the invention a variable stiffness catheter comprises an outer layer, an inner layer, a first coil, and a second coil. The outer layer has a bore with an inner surface and the inner layer is disposed within the bore. The inner layer is coaxial with the outer layer and has an outer surface. The first coil has a first helical axis coaxial with the inner layer and comprises a first wire wrapped around the first helical axis in a first plurality of turns disposed between the inner surface and the outer surface. The first coil is fixed in place relative to the outer layer and the inner layer. The second coil has a second helical axis coaxial with the inner layer and comprises a second wire wrapped around the second helical axis in a second plurality of turns disposed between the first inner surface and the second inner surface. The second plurality of turns are disposed between the first plurality of turns and the second coil is rotatable about the second helical axis relative to the outer layer, the inner layer, and the first coil.

In another embodiment a variable stiffness catheter comprises a wall, a first coil, a helical channel in the wall, and a second coil. The wall has an inner surface and an outer surface and the first coil is disposed in the wall between the inner surface and the outer surface. The first coil is fixed in place relative to the wall. The helical channel is disposed in the wall between the inner surface and the outer surface between adjacent turns of the first coil and the second coil is disposed in the helical channel.

BRIEF DESCRIPTION OF THE DRAWINGS

To further clarify the above and other advantages and features of the one or more present inventions, reference to specific embodiments thereof are illustrated in the appended drawings. The drawings depict only typical embodiments and are therefore not to be considered limiting. One or more embodiments will be described and explained with additional specificity and detail through the use of the accompanying drawings in which.

The drawings are not necessarily to scale.

DETAILED DESCRIPTION

As used herein, "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" means A alone, B alone, C alone, A and B together, A and C together, B and C together, or A, B and C together.

Various embodiments of the present inventions are set forth in the attached figures and in the Detailed Description as provided herein and as embodied by the claims. It should be understood, however, that this Detailed Description does not contain all of the aspects and embodiments of the one or more present inventions, is not meant to be limiting or restrictive in any manner, and that the invention(s) as disclosed herein is/are and will be understood by those of ordinary skill in the art to encompass obvious improvements and modifications thereto.

Additional advantages of the present invention will become readily apparent from the following discussion, particularly when taken together with the accompanying drawings.

In the following discussion, the terms "distal" and "proximal" will be used to describe the opposing axial ends of the inventive balloon catheter, as well as the axial ends of various component features. The term "distal" is used in its conventional sense to refer to the end of the apparatus (or component thereof) that is furthest from the operator during use of the apparatus. The term "proximal" is used in its conventional sense to refer to the end of the apparatus (or component thereof) that is closest to the operator during use. For example, a catheter may have a distal end and a proximal end, with the proximal end designating the end closest to the operator heart during an operation, such as a handle, and the distal end designating an opposite end of the catheter, such as treatment tip. Similarly, the term "distally" refers to a direction that is generally away from the operator along the apparatus during use and the term "proximally" refers to a direction that is generally toward the operator along the apparatus.

Figure 1:
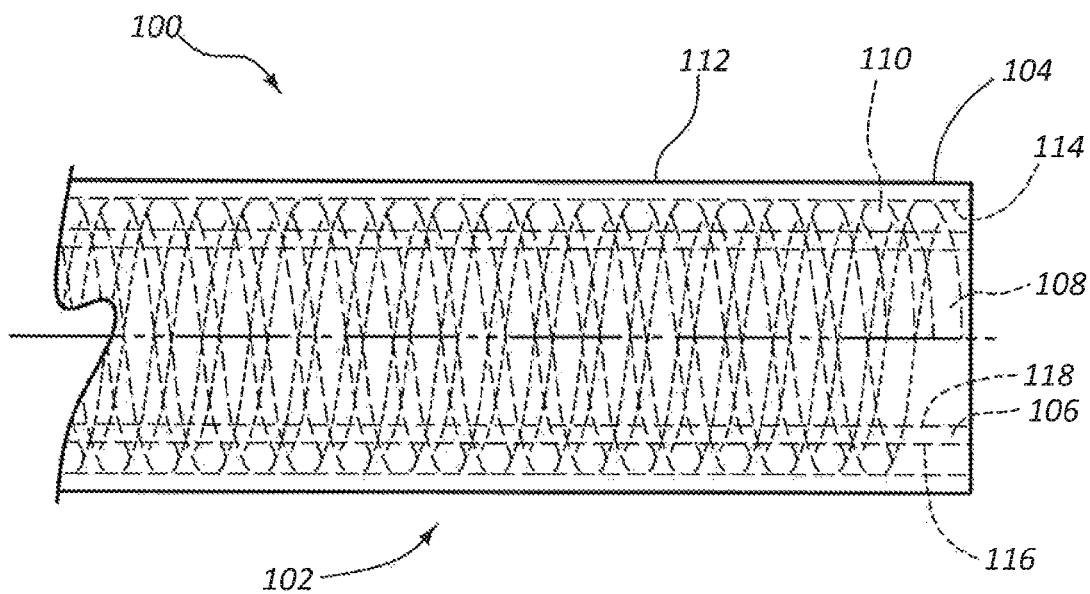
FIG. 1 is a side view of the distal end of variable stiffness catheter.
Figure 2:
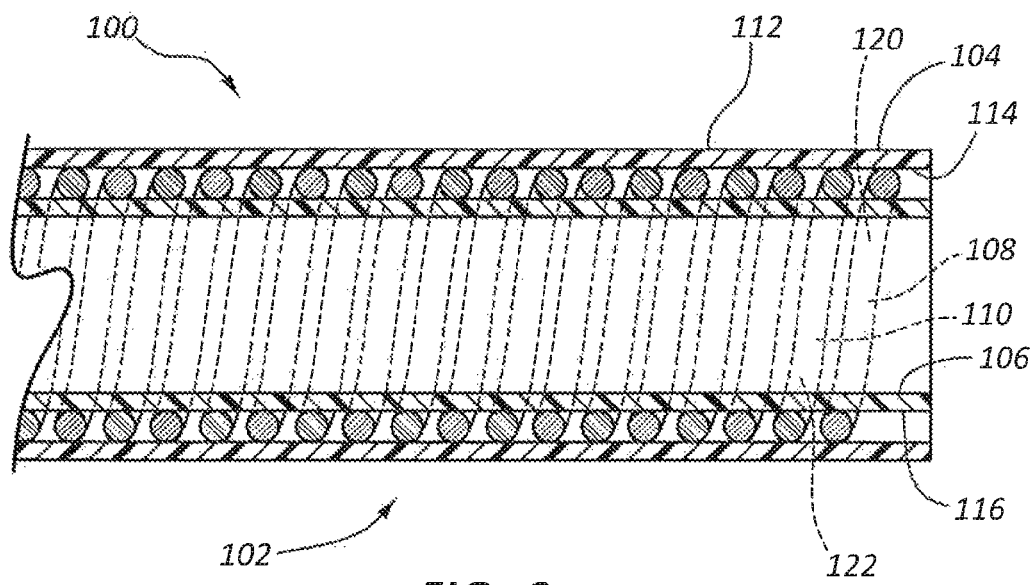
FIG. 2 is a longitudinal cross section of the distal end of the variable stiffness catheter of FIG. 1.

FIG. 1 illustrates a side view of a distal end 102 of a variable stiffness catheter 100. FIG. 2 is a cross-sectional view of the variable stiffness catheter 100 of FIG. 1. The variable stiffness catheter 100 is comprised of an outer layer 104, an inner layer 106, a first coil 108, and a second coil 110.

The outer layer 104 has an outer surface 112 and an inner surface 114 defining a bore. The inner layer 106 is disposed within the bore of the outer layer 104 and is coaxial with the outer layer 104. The inner layer 106 has an outer surface 116 and an inner surface 118 defining a bore of the variable stiffness catheter 100. The outer surface 116 of the inner layer 106 faces the inner surface 114 of the outer layer 104.

Figure 3:
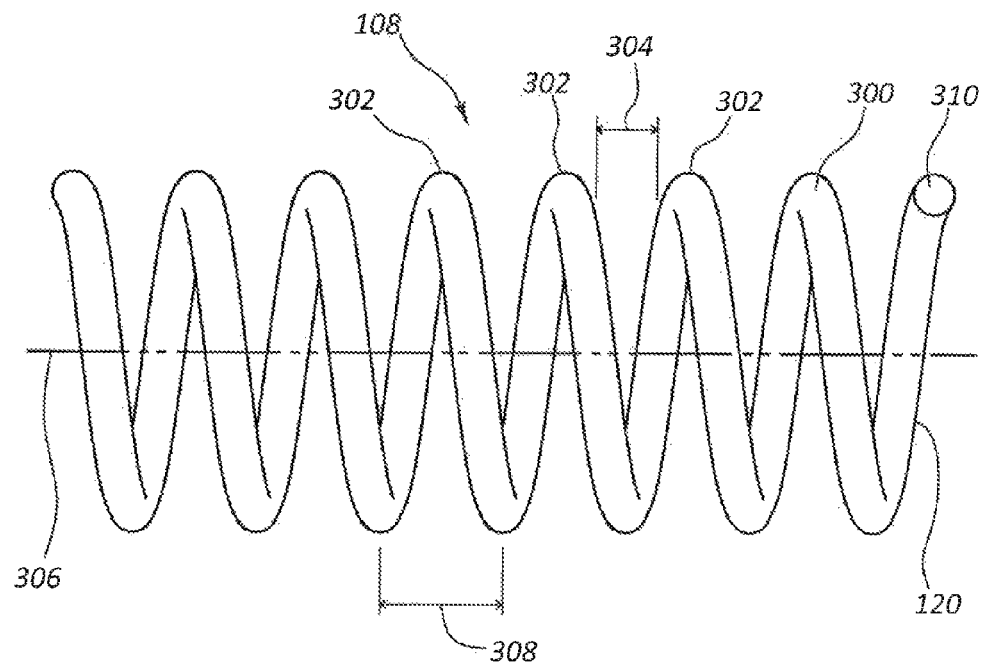
FIG. 3 is a side view of the distal end of a first coil.

FIG. 3 is a side view of the first coil 108. The first coil 108 is comprised of a first wire 120 wound into a first helix 300 about a first helical axis 306. The first helix 300 has a plurality of turns 302 having a gap 304 between adjacent turns 302. Each turn 302 of the first helix 300 is separated by a pitch 308 distance. The first wire 120 has a cross section 310 defined by a plane cutting through the first wire 120 perpendicular to its axis. In the example of FIG. 3 the cross section 310 is a circle, although other patterns are possible. In other embodiments the cross section 310 may be rectangular, square, or other shape. In some embodiments the cross section 310 may vary along the length of the wire. The first wire 120 may be comprised of stainless steel, although other materials such as nickel titanium alloys and stiff polymers are suitable for use as the wire.

Returning to FIG. 2, the first coil 108 is disposed between the inner surface 114 of the outer layer 104 and the outer surface 116 of the inner layer 106. The first coil 108 is fixed in place relative to the outer cylindrical layer 104 and the inner cylindrical layer 106. In some embodiments the first coil 108 may be bonded to the inner surface 114 of the outer layer 104 and the outer surface 116 of the inner layer 106 to fix the first coil 108 in place.

Figure 4:
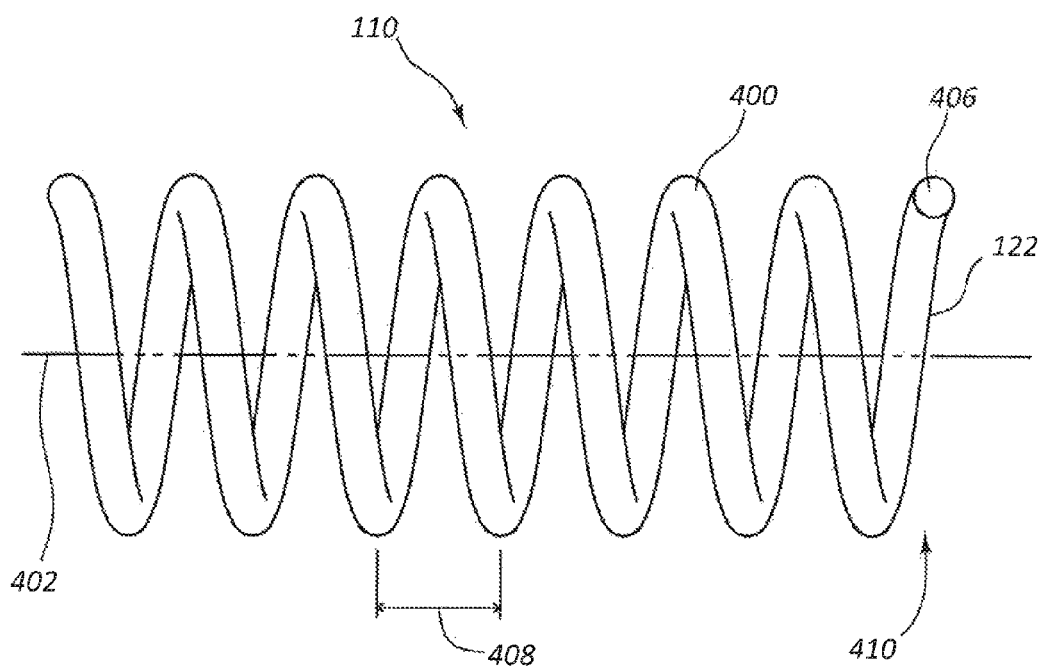
FIG. 4 is a side view of the distal end of a second coil.

FIG. 4 is a side view of the second coil 110. The second coil 110 is comprised of a second wire 122 wound into a helix 400 about a second helical axis 402. The second coil 110 has a pitch 408 that is substantially the same as the pitch 308 of the first coil 108, such that the second wire 122 may be disposed in the gap 304 between adjacent turns 302 of the first coil 108 without interfering with the first wire 120. The second coil 110 is disposed between the inner surface 114 of the outer layer 104 and the outer surface 116 of the inner layer 106 with the second wire 122 lying in the gap 304 between adjacent turns 304 of the first coil 108. The second coil 110 is not fixed relative to the outer layer 104 and the inner layer 106 and is constrained in movement by the first wire 108, the outer layer 104, and the inner layer 106.

The second coil 110 is rotatable about the second helical axis 402 relative to the outer layer 104, the inner layer 106, and the first coil 108. Like a screw, when the second coil 110 rotates about the second helical axis 402, the second coil 110 translates axially relative to the first coil 108. Rotating the second coil 110 in a first direction will cause the second coil 110 to translate distally, while rotation of the second coil 110 in the opposite direction will cause the second coil 110 to translate proximally.

The second wire 122 may have a second cross section 406 that is substantially the same as the first cross section 306 as shown in FIG. 4. In other embodiments, the cross section 406 of the second wire 122 is shorter in a radial direction than the cross section 306 of the first wire 120. Having a shorter cross section 406 reduces the resistance to rotation of the second coil 110 relative to the inner surface 114 of the outer layer 104 and the outer surface 116 of the inner layer 106. The second wire 122 may be comprised of stainless steel, although other materials such as nickel titanium alloys and stiff polymers. In some embodiments, the second wire 122 may comprise a different material than the first wire 120. For example, the first wire 120 could be comprised of a nickel titanium alloy and the second wire 122 could be comprised of stainless steel.

The variable stiffness catheter 100 has a stiffness along its length that is equal to the combined stiffness of the inner layer 106, the outer layer 104, the first coil 108, and the second coil 110. When the second coil 110 is moved proximally through the rotation of the second coil 110, a region of reduced stiffness is present in the region distal to the distal end 410 of the second coil 110. Thus, when the second coil 110 is retracted proximally, the variable stiffness catheter 100 has a first region 502 proximal to the distal end 410 of the second coil 110 having a higher stiffness and a second region 500 distal to the distal end 410 of the second coil 110 having a lower stiffness, as shown in FIG. 5.

Figure 5:
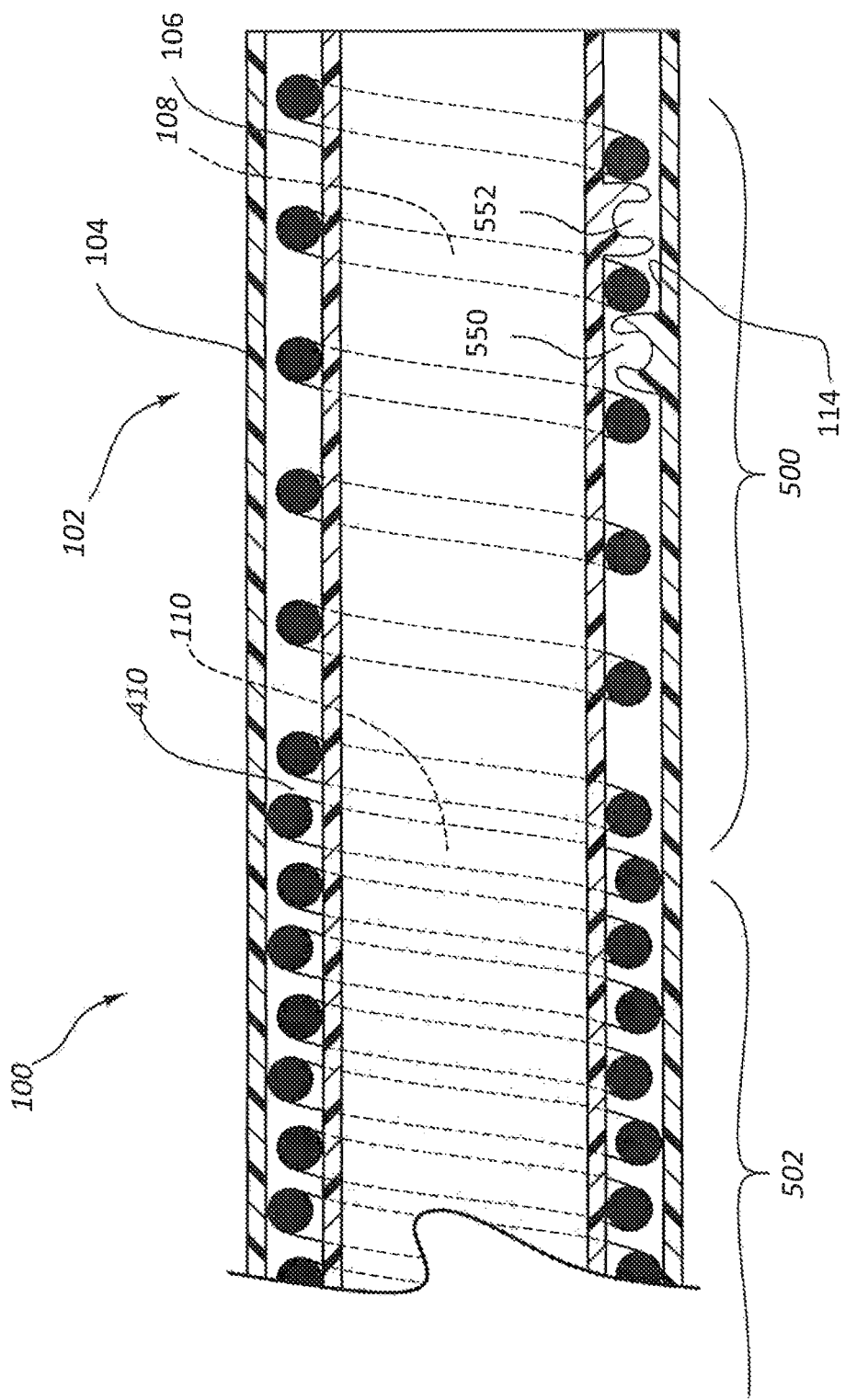
FIG. 5 is a longitudinal cross section of the distal end of the variable stiffness catheter of FIG. 1 with the second coil moved axially.

FIG. 5 shows a longitudinal cross section of the distal end 102 of the variable stiffness catheter 100 with the second coil 110 being displaced proximally relative to the first coil 108. The second region 500 of the variable stiffness catheter 100 can be lengthened by further moving the distal end 410 of the second coil 110 distally. Similarly, the length of the second region 500 can be increased by moving the distal end 410 of the second coil 110 distally. For example, it may be useful to have a flexible tip when traversing a tortuous vascular system, and then switch to a more rigid tip once past the tortuous vascular system. This would be accomplished by moving the distal end 410 of the second coil 110 proximally for use when traversing the tortuous vascular system and then advancing the distal end 410 of the second coil 110 once past the tortuous vascular system.

Figure 6:
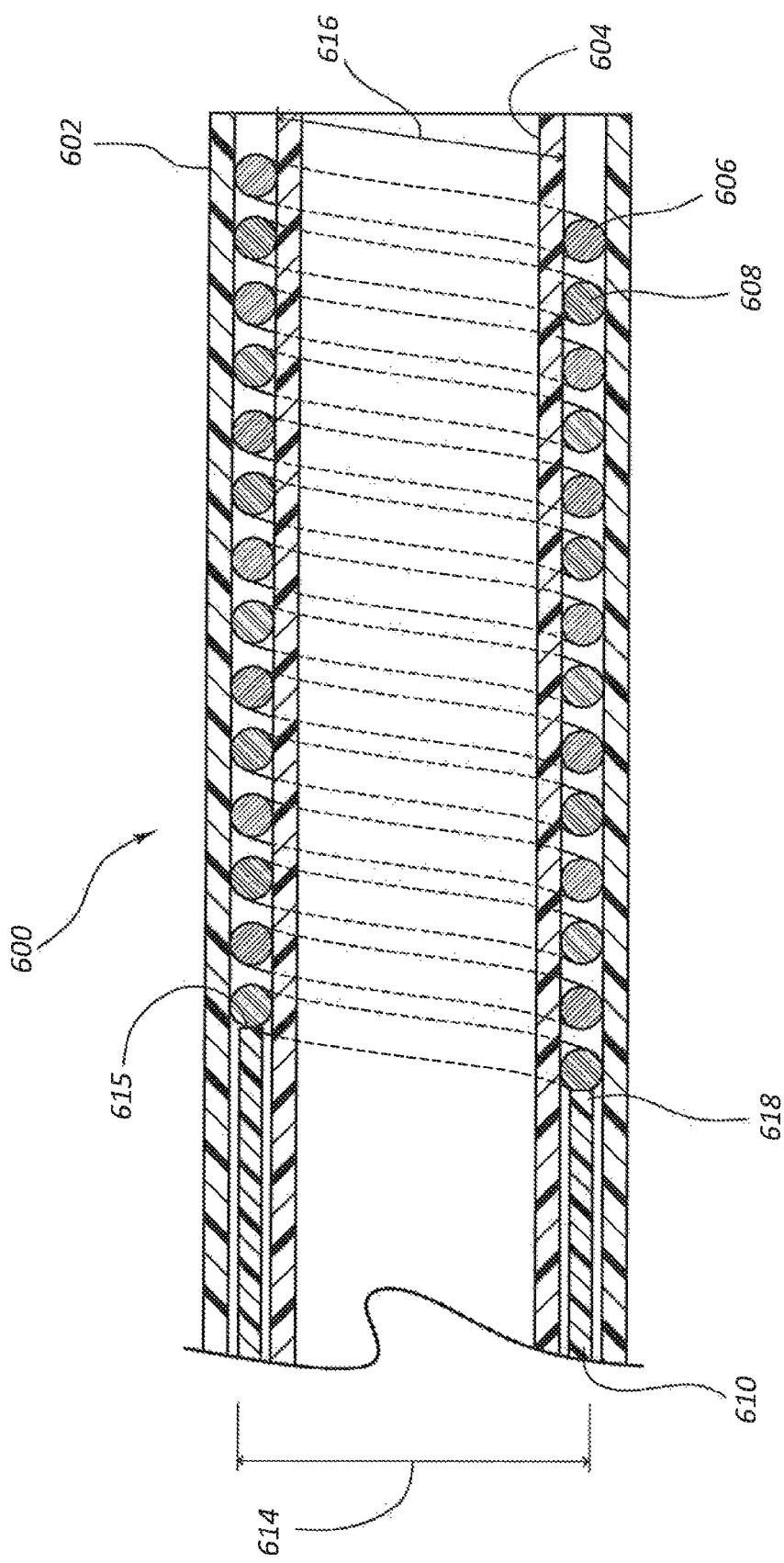
FIG. 6 is a longitudinal cross section of the distal end of a variable stiffness catheter having a tube proximal to the second coil.

FIG. 6 illustrates another embodiment of a variable stiffness catheter 600. This embodiment is similar to the previously described embodiment of FIG. 1 and is comprised of an outer layer 602, an inner layer 604, a first coil 606, a second coil 608, and a tube 610. A distal and 618 of the tube 610 is coupled to a proximal end 615 of the second coil 608. In the embodiment of FIG. 6, the tube 610 has an outside diameter 614 greater than an inside diameter 616 of the first coil 606. To avoid interference between the first coil 606 and the tube 610, first coil 606 ends prior to the distal end 618 of the tube 610. In other embodiments, the tube 610 may have an outside diameter 614 less than the inside diameter 616 of the first coil 606 such that the tube 610 is able to pass within the first coil 606. The tube 610 has a greater torsional stiffness than the second coil 608 and is used to transmit torque over a greater distance than the second coil 608 alone. The proximal end (not shown) of the tube 610 is disposed proximate the proximal end of the variable stiffness catheter 600 and transmits relative rotation of the tube 610 near the proximal end of the variable length catheter 600 to the second coil 608 disposed at the distal end of the variable length catheter 600. The tube 610 may be comprised of stainless steel, although other materials such as nickel titanium alloys and stiff polymers are suitable for use as the tube.

Figure 7:
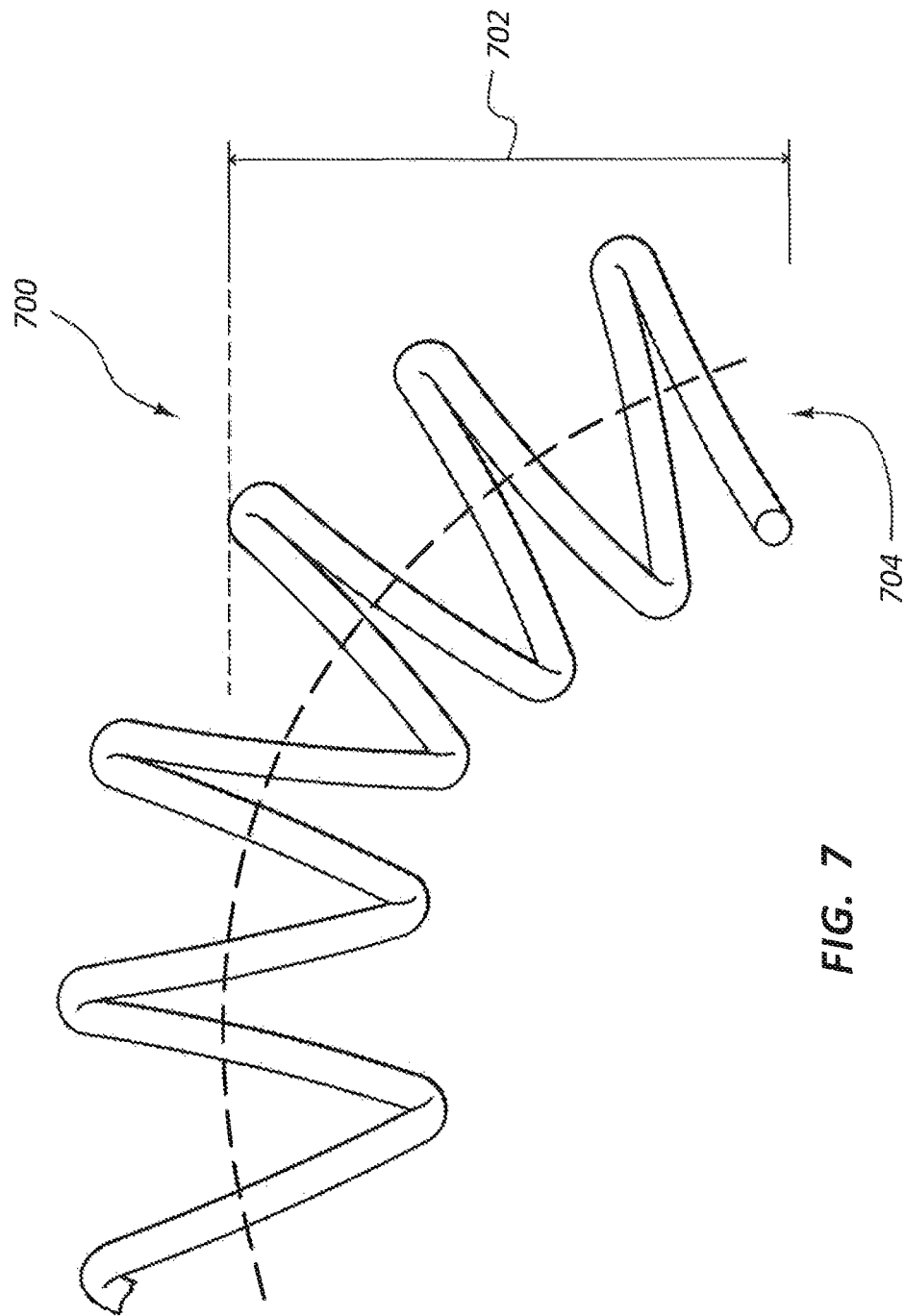
FIG. 7 is a side view of an embodiment of the first coil having a lateral bias at the distal end.

FIG. 7 illustrates a longitudinal cross section of an alternative embodiment of the first coil 700. In this embodiment the first coil 700 is self-biased to have a lateral displacement 702 at its distal end 704. The second coil is biased to be substantially straight. When the distal end of the second coil is proximate the distal end 704 of the first coil 700, the variable stiffness catheter 100 is substantially straight. As the second coil is retracted proximally, the bias of the first coil 700 causes the distal end of the variable stiffness catheter 100 to deflect in the direction of the bias. This allows the variable stiffness catheter 100 to have a variable curve depending on the needs of the user.

In some embodiments, as partially shown in FIG. 5, the inner surface 114 of the outer layer 104 may extend into the gap between adjacent turns of the first coil 108. In such embodiments the inner surface 114 of the outer layer 104 may have a helical groove 550 in the gap for receiving the second coil 110. In other embodiments, the outer surface of the inner layer 106 may extend into the gap between adjacent coils of the first coil 108. In such embodiments, the inner layer 106 may have a helical groove 552 in the gap for receiving the second coil 110.

In another embodiment the inner layer and the outer layer may be comprised of the same material and form an integral wall having the coils disposed within the wall. In such embodiments the first coil is fixed within the wall and the second coil is free to rotate relative to the first coil and the integral wall. The helical channel is formed in the integral wall in the gap between adjacent turns of the first coil. The second coil travels in the helical channel when rotated relative to the first coil and the integral wall. The channel may be formed by coating the second coil with a release compound allowing the integral wall to be formed with the second wire in place. Because the second coil is coated with the release compound it may be rotated within the integral wall since it is not adhered to the integral wall lie the first coil.

In some embodiments a helical plug having a cross section larger than the second coil may be coated with a release compound when the integral wall is formed. The helical plug may then be removed leaving a channel having a cross section greater than the second coil. The second coil may then be threaded into the helical channel left by the helical plug.

Embodiments of the invention have been primarily described in terms of a single lumen catheter. It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

What is claimed:

1. A method of varying the stiffness of a catheter, comprising:
guiding a distal end of a variable stiffness catheter to a target location, the variable stiffness catheter comprising an outer layer, an inner layer disposed within the outer layer and being coaxial with the outer layer, a first coil comprising a first wire wrapped around the inner layer, and a second coil comprising a second wire wrapped the inner layer between turns of the first coil; and
rotating the second coil causing the second coil to move axially between the inner and outer layer, thereby changing the stiffness at the distal end of the variable stiffness catheter.

2. The method of claim 1, wherein the rotation of the second coil causes the distal end of the second coil to move distally, thereby increasing the stiffness of the catheter at the distal end.

3. The method of claim 2, wherein the distal end of the variable stiffness catheter is guided through a tortuous vascular system to the target area with the second coil in a retracted state, and wherein the method further comprises guiding the distal end of the variable stiffness catheter to a second target location after increasing the stiffness of the catheter at the distal end.

4. The method of claim 1, wherein the rotation of the second coil causes the distal end of the second coil to move proximally, thereby decreasing the stiffness of the variable stiffness catheter at the distal end.

5. A method of guiding a variable stiffness catheter through a vascular system, comprising:
advancing a distal end of a variable stiffness catheter within a vascular system, the variable stiffness catheter comprising an outer layer, an inner layer disposed within the outer layer and being coaxial with the outer layer, a first coil self-biased to have a lateral displacement at a distal end, the first coil comprising a first wire wrapped around the inner layer, and a second coil comprising a second wire wrapped the inner layer between turns of the first coil, the second coil being self-biased to a straight configuration;
encountering a turn within the vascular system; and
rotating the second coil causing the distal end of the second coil to retract relative to the distal end of the first coil and allowing the self-bias of the first coil to deflect laterally.

6. The method of claim 5, further comprising:
advancing the distal end of the variable stiffness catheter into the turn with the laterally deflected first coil; and
encountering a straight portion within the vascular system; and
rotating the second coil causing the distal end of the second coil to advance relative to the distal end of the first coil and overcoming the self-bias of the first coil to return the distal end of the variable stiffness catheter to a straight configuration.

* * * * *